(12) United States Patent
Bergquist

(10) Patent No.: US 6,919,089 B2
(45) Date of Patent: Jul. 19, 2005

(54) PUCKER RESISTANT COSMETIC SACHET

(75) Inventor: Paul Roland Bergquist, Southport, CT (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 271 days.

(21) Appl. No.: 10/166,099

(22) Filed: Jun. 10, 2002

(65) Prior Publication Data

US 2003/0003136 A1 Jan. 2, 2003

Related U.S. Application Data

(63) Continuation-in-part of application No. 10/079,290, filed on Feb. 19, 2002, now abandoned.

(51) Int. Cl.[7] .............................................. A01N 25/34
(52) U.S. Cl. ........................................ 424/402; 424/401
(58) Field of Search .............................. 424/404, 402, 424/401

(56) References Cited

U.S. PATENT DOCUMENTS

| | | | |
|---|---|---|---|
| 3,485,706 A | 12/1969 | Evans | |
| 4,935,158 A * | 6/1990 | Aszman et al. | 15/104.93 |
| 5,744,149 A | 4/1998 | Girardot | |
| 5,980,931 A | 11/1999 | Fowler et al. | |
| 6,063,390 A * | 5/2000 | Farrell et al. | 424/404 |
| 6,136,768 A | 10/2000 | Dawson et al. | |
| 6,191,100 B1 | 2/2001 | Askew et al. | |
| 6,280,757 B1 | 8/2001 | McAtee et al. | |
| 6,300,302 B1 | 10/2001 | Brooker et al. | |
| 6,313,086 B1 | 11/2001 | Askew et al. | |
| 2003/0104036 A1 | 6/2003 | Gregoire | |

FOREIGN PATENT DOCUMENTS

| | | |
|---|---|---|
| EP | 0 836 842 | 10/1996 |
| EP | 0 836 842 B1 * | 4/1998 |
| EP | 1 091 035 | 10/2000 |
| WO | 97/00771 | 1/1997 |
| WO | 00/07561 | 2/2000 |
| WO | 00/42961 | 7/2000 |
| WO | 01/08542 | 2/2001 |
| WO | 01/08640 | 2/2001 |
| WO | 01/08641 | 2/2001 |
| WO | 01/08655 | 2/2001 |
| WO | 01/08656 | 2/2001 |
| WO | 01/08657 | 2/2001 |
| WO | 01/08658 | 2/2001 |
| WO | 01/45616 | 6/2001 |
| WO | 01/56542 | 8/2001 |

* cited by examiner

Primary Examiner—Thurman K. Page
Assistant Examiner—Sharon Howard
(74) Attorney, Agent, or Firm—Milton L. Honig

(57) ABSTRACT

An article is provided for cleansing surfaces, the article includes a curvilinear pouch formed from a plurality of walls, at least one of the walls being water permeable, and at least one of the walls being formed from at least one web of non-woven entangled fibers, the fibers being entangled in a direction perpendicular to a major longitudinal axis of the web. An effervescent cleanser composition which is an anhydrous dry solid activatable by water to generated gases is held within the pouch, and upon generation of gases the pouch walls billow outwardly. Orientation of the entangled fibers in the direction of the minor axis minimizes puckering of the article in use.

9 Claims, 2 Drawing Sheets

PUCKER RESISTANT COSMETIC SACHET

CROSS REFERENCES

This application is a continuation-in-part of Ser. No. 10/079,290, filed Feb. 19, 2002, now abandoned, from which priority is claimed.

BACKGROUND OF THE INVENTION

1. Field of the Invention

The invention concerns inflatable sachets containing an effervescent dry powder activatable to release gases and thereby outwardly billow the sachet.

2. The Related Art

Cleansing products have traditionally been marketed in the form of bar soaps, shower gels and mousses, the lather being generated by mechanical and aerosol dispensers. Mechanical implements have been used by consumers to assist in lather formation and physical removal of dirt through scrubbing. Wash cloths have been the implement of choice throughout recent history.

New formats for cleansing hold great consumer appeal. For instance, surfactant and conditioner compositions have been layered into apertured wipes such as disclosed in U.S. Pat. No. 6,280,757 (McAtee et al.). Open-mesh sponges such as described in U.S. Pat. No. 6,066,607 (Gordon et at.) have assisted in generating foam from shower gels thereby improving speed and quality of lathering.

U.S. Pat. No. 5,980,931 (Fowler et al.) describes a substantially dry, disposable personal care article wherein a surfactant system is dried onto a water-insoluble non-woven or similar substrate. A second generation of dual layered towelette has been reported. See WO 00/42961 (Smith), WO 01/08542 (Cen et al.), WO 01/08640 (Smith et al.), WO 01/08641 (Lorenzi et al.), WO 01/08655 (Phipps et at.), WO 01/08656 (Lorenzi et at.), WO 01/08657 (Lorenzi et at.) and WO 01/08658 (Cawkwell et at.) all describing disposable personal cleansing towelettes with lathering surfactant on at least a two layer cloth with one layer being a high loft substrate. Consumers are expected to place the towelette under water to generate a surfactant lather.

Another approach is described in U.S. Pat. No. 6,063,390 (Farrell et al.) which reports a wiping article structured as a pouch containing an effervescent cleanser composition. At least one of the pouch walls are water permeable. When wetted with water, the composition components of an acid material and an alkaline material effervesce to generate carbon dioxide, as well as exuding copious amounts of lather from a surfactant component. A plumped "pillow" arises from the effervescent action.

EP 0 836 842 B1 (Moore et al.) discloses oval shaped disposable non-woven cleaning articles. These are formed of hydro-entangled fibers wherein entanglement is oriented in a direction parallel to the major axis of the oval.

Elongate shaped pouches are particularly suitable for gripping; they tend to more ergonomically fit within the hand. For the present invention, an effervescent sachet system was sought which would be easily grippable.

A problem encountered with sachets formed from non-woven materials is their tendency to pucker. When the dry effervescent composition is activated with water, the resultant evolution of gases inflates the sachet into a bulging pillow arrangement. Deformation of the sachet watts results in a substantial pucker of the pillow configuration. Both for aesthetic and ergonomic reasons, the pucker is undesirable.

Accordingly, it is an object of the present invention to provide a cosmetic article with an activatable effervescent cleansing system which upon inflation by effervescent gases causes the article to inflate but avoids deformation and puckering of the article.

It is to be noted that the subsequently described invention is broader than the objects or technical problems it is directed to solve.

SUMMARY OF THE INVENTION

An article is provide for cleansing surfaces, the article including:
- a curvilinear pouch formed from a plurality of walls, at least one of the walls being water permeable, and at least one of the walls being formed from at least one web of non-woven entangled fibers, the fibers being entangled in a direction perpendicular to a major longitudinal axis of the web; and
- an effervescent cleanser composition which is an anhydrous dry solid activable by water to generate gases, the composition being held within the pouch, and upon generation of gases the pouch walls billowing outwardly.

DETAILED DESCRIPTION OF THE DRAWING

Further objects, features and advantages of the present invention will become more readily apparent from consideration of the drawing, in which.

DETAILED DESCRIPTION OF THE INVENTION

Now it has been found that proper orientation of fibers in a non-woven web forming a wall of the pouch can avoid the problem of puckering. Upon release of gases through water activation of the effervescent composition, the walls of the pouch billow outwardly. Directed orientation of the entangled fibers forming a web which is at least part of the pouch wall allows the system to stretch thereby avoiding deformation and any substantial puckering.

Figure 1:
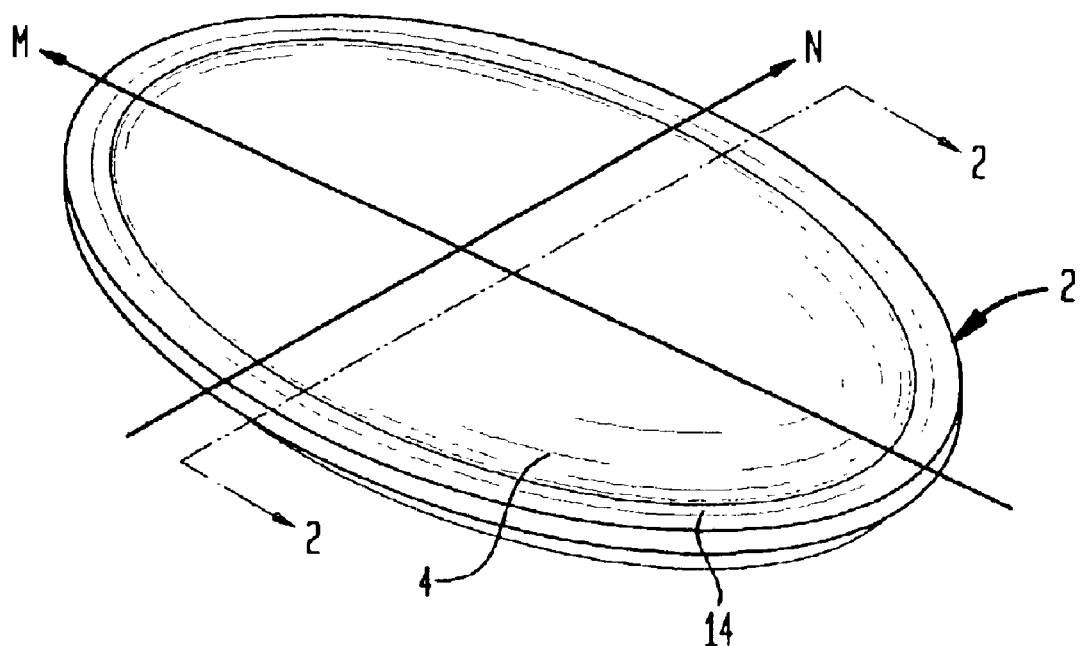
FIG. 1 is a plan perspective view of a first embodiment in the form of an oval sachet.

FIG. 1 illustrates a first embodiment wherein the pouch is oval shaped.

Figure 2:
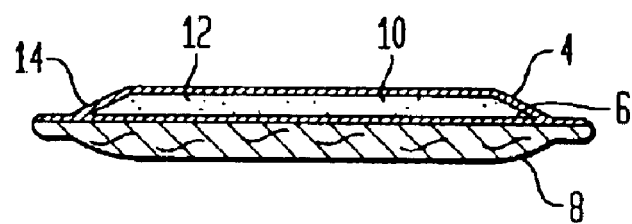
FIG. 2 is a cross-section along line 2—2 of the first embodiment shown in FIG. 1.

The pouch 2 has walls formed by a first spun lace web 4 and a second meltblown composite web 6, the latter being bonded to a high loft sheet 8. The webs forming webs 4 and 6 are non-woven entangled fiber matrices. FIG. 2 best illustrates by cross-section the several webs constituting the walls. Chamber 10 formed between the first and second webs 4, 6 serves to confine a powdered effervescent composition 12. Webs 4 and 6 are ultrasonically sealed along a circumferential track 14 to insure no loss of the powdered composition.

Pouch 2 is defined by a major axis M oriented in a longitudinal direction and a minor axis N oriented in a Lateral direction, the major axis being longer than the minor one.

Figure 3:
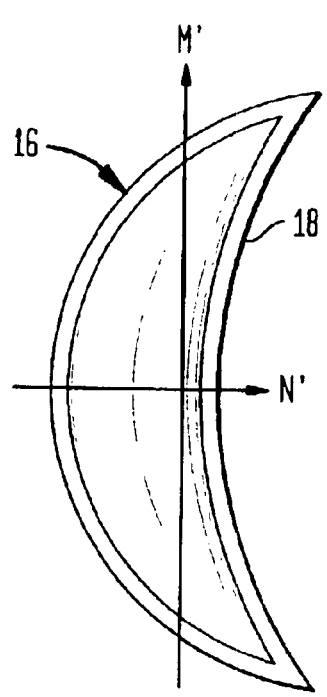
FIG. 3 is a front elevational view of a second embodiment of a sachet according to the present invention.

FIG. 3 is a second embodiment of the invention. It illustrates a crescent-shaped sachet 16. Major and minor axes, (M' and N'), are outlined on the Figure.

Figure 4:
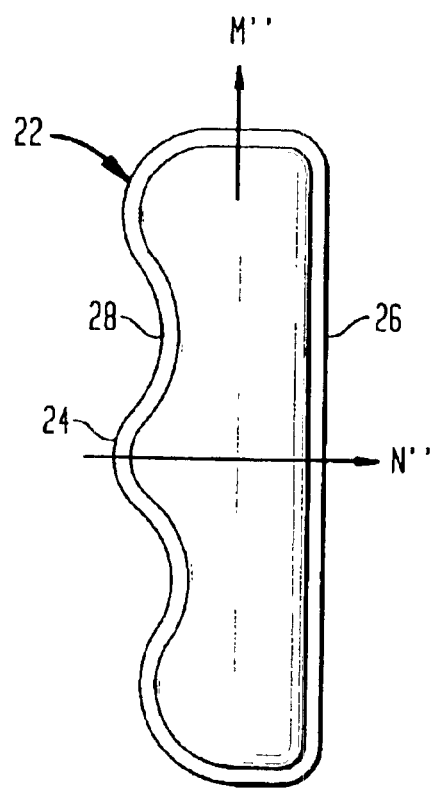
FIG. 4 is a front elevational view of a third embodiment of a sachet according to the present invention.

FIG. 4 illustrates a third embodiment according to the present invention. Sachet 22 along one edge has a sinusoidal shape 24 and along an opposite edge a straight configuration 26. Major and minor axes are identified as M" and N".

FIGS. 3 and 4 provide particularly useful curvilinear edges because of their more grippable and less slip-prone configuration relative to that of an oval. Yet the problem of puckering is particularly aggravated in configurations having concave edges such as identified by 18 and 28.

Figure 5:
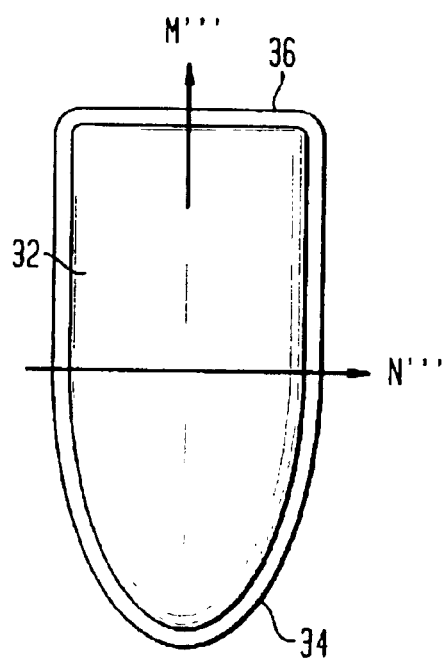
FIG. 5 is a front elevational view of a fourth embodiment of a sachet according to the present invention.

FIG. 5 illustrates a fourth embodiment. Sachet 32 at the ends of the major axis M''' has a straight edge 36 and at opposite ends a rounded edge 34. Minor axis N''' traverses the major axis.

Copious foam is generated when pouch 2 is wetted with water, much in the same manner as a toilet bar is lathered. Physically, the pouch is constructed in an oval shape with a size fittable within a human hand thereby simulating a toilet bar.

The term "major axis" refers to the longitudinal direction or length and is defined as the direction parallel to the longitudinal center line of the sachet. Normally the major axis coincides with the material direction (MD) along which the web is produced. In other words, as fibers are laid down they are conveyed as a web away from the depositing source in a MD movement. The term "minor axis" refers to the lateral direction or width and is defined as the direction perpendicular to the longitudinal center line of the sachet. Normally the minor axis coincides with the cross direction (CD) arranged orthogonal to the MD along which the web is produced.

Tensile Strength of nonwovens is ordinarily strongest in the machine direction. Entanglement oriented webs of the present invention seek to improve strength in the CD relative to the MD length. However, the resultant oriented webs will not necessarily exhibit higher tensile strength in the CD than MD length; but tensile strength differences will have been narrowed. For instance, a spun lace fabric may be formed from fiber deposition that is CD to MD in a tensile strength ratio of circa 1:4. Subsequent hydroentanglement orientation enhances the ratio to circa 1:2. Preferably orientation of entangled fibers will increase tensile strength by at least 20%, more preferably by at least 50%, and optimally by at least 100% in CD versus MD value.

Typical dimensions for the major axis may range from about 20 mm to about 300 mm, preferably from about 30 to about 100 mm. Dimensions of the minor axis may range from about 30 to about 85 mm, preferably from about 20 to about 50 mm.

Orientation of the fibers of the present invention is not limited to any particularly technique. In fact, any technique known in the art can be employed to gain the desired orientation effect.

The pouch comprises at least one web of entangled fibers. The entangled fibers are entangled in a direction perpendicular to the major axis of the pouch. The preferred method of manufacturing entangled fibers utilizes a process known as hydroentangling. A hydroentangled web that is strong and durable is produced by traversing material fibers with high energy jet streams of water in order to interlock the fibers. Other high pressure fluids can be used in place of water.

Although hydroentangling is preferred as the method of producing the entangled web, other methods can alternatively be employed. Needlepunching is an example of a method which can be employed. In this method, barbed needles are punched through the web, hooking tufts of fibers across it and thereby bonding it in the needlepunched areas.

Another method which can be utilized is thermal bonding, in which the fibers are of thermoplastic material, or have an outer layer of thermoplastic material, and are bonded together in discrete spots by heat. A web produced in this way is unlikely to be as soft as one produced by hydroentangling, or needlepunching, and it may have a substantial proportion of completely loose fibers. Yet another method involves wet-laying a mixture of fibers and chemical binder, somewhat in the manner employed, for example, in paper making. Yet a further method is carding, in which staple fibers are opened, cleaned, aligned and formed into a continuous unbonded web. White hydroentangling, and chemically, thermally, mechanically bonded materials and carded materials are representative of the technologies which can be incorporated in the present invention, these do not exhaust all the possibilities. Other technologies such as embossing, creping and aperturing can be incorporated into the manufacture of the pouch.

Web 6 may be a single meltblown web but preferably it is a combination of several layers forming a composite web. One embodiment utilizes the three layers of spunbond/meltblown/spunbond (SMS) and another utilizes four layers representing spunbond/meltblown/meltblown/spunbond (SMMS) construction. In these systems the meltblown fibers are very compact and act as a barrier against loss of powder. The spunbond layers are provided for strength and softness.

The meltblown web can be any meltblown web made from a thermoplastic polymer having a melting point greater than about 50° C. A preferred polymer is polypropylene, which is the most commonly used polymer for making meltblown webs. Other suitable polymers include poly (butylene terephthalate), polycaprolactam, poly(ethylene terephthalate) and polyethylene.

The process for making meltblown webs is well known in the art and is used extensively for manufacturing a wide variety of commercial nonwoven products. Representative examples of the meltblowing process are described in U.S. Pat. No. 3,978,185 to Buntin et al. dated Aug. 31, 1976; U.S. Pat. No. 4,298,649 to Meitner dated Nov. 3, 1981; and U.S. Pat. No. 4,100,324 to Anderson et al. dated Jul. 11, 1978, all herein incorporated by reference. It will be appreciated, however, that other meltblowing processes will produce webs suitable for purposes of this invention. The meltblown web can be combined or laminated to other supporting webs, such as spunbonded webs, in order to impart strength or other attributes to the product.

The basis weight for a single sheet of the meltblown base webs of this invention can range from about 20 to about 300 grams per square meter. Preferably the basis weight will be from about 80 to about 250, and most preferably from about 100 to about 200 grams per square meter.

Spunbonding entails extruding a multiplicity of continuous thermoplastic polymer strands through a multiplicity of die orifices in a downward direction onto a moving surface where the extruded strands are collected in randomly distributed fashion. The randomly deposited strands are then bonded together in a heated nip to provide sufficient integrity to the resulting nonwoven web of continuous fibers. Spunbonded webs are characterized by a high strength/weight ratio, isotropic strength, high porosity, and good abrasion resistance.

Meltblowing differs from spunbonding in that the extruded polymer strands are broken up and dispersed into individual fibers by a forced air stream before being deposited onto the collecting surface. In addition, the fibers are substantially cooled by the air so that they do not significantly crystallize and/or bond together. Bonding of the web to retain integrity and strength occurs as a separate downstream operation.

A most preferred material for the second web 6 is a non-woven meltblown/spunbond substrate available from the Polyprop Corporation.

The first web 4 preferably is either a spun lace or a carded/chemically bonded non-woven water-insoluble material. Particularly preferred is a cloth NC008 (Image Spun Lace) available from the PGI Corporation.

When present, a high loft sheet may be utilized as the water-permeable wall. As used herein, "high loft" means that the sheet has a density of from about $0.00005$ g/cm$^3$ to about $0.1$ g/cm$^3$, preferably from about $0.001$ g/cm$^3$ to about $0.09$ g/cm$^3$ and a thickness of from about 0.1 cm to about 5 cm.

As used herein, "nonwoven" means that the layer does not comprise fibers which are woven into a fabric. The term "curvilinear" means that at least one edge defining the pouch is a curved surface. Preferably the pouch exhibits no squared corners.

For purposes of this invention, the most preferred high loft material is a needle punched composite sold by Union Wadding Corporation.

Sachets of the present invention may be produced by depositing a charge of effervescent powder through a funnel nozzle onto an oriented nonwoven web as it moves in a horizontal manner. Downstream a similarly oriented hydroentangled web is unfurled from a roll and travels in a direction above and parallel to that of the first web. The parallel webs and deposited effervescent powder then pass underneath a stamping station which heat seals in an oval pattern the first and second webs together with the effervescent powder charge between the web walls. Subsequently, a cutter die punches out the heat sealed oval article.

One or more of the articles may then be packaged within a moisture impermeable outer package such as a laminated foil bag to prevent activation of the effervescent system during storage.

Ultrasonic welding may be employed as an alternative to heat-sealing of the first and second substrates together. Thread stitching, glue application or other closure mechanisms may also be utilized.

A first component of compositions 12 within the pouch is that of an acidic material. Suitable for this purpose are any acids, and preferably those present in dry solid form. Especially appropriate are $C_2$–$C_{20}$ organic mono- and polycarboxylic acids and especially alpha- and beta-hydroxycarboxylic acids; $C_2$–$C_{20}$ organophosphorus acids such as phytic acid; $C_2$–$C_{20}$ organosulfur acids such as toluene sulfonic acid; and peroxides such as hydrogen peroxide. Typical hydroxycarboxylic acids include adipic, glutaric, succinic, tartaric, malic, maleic, lactic, salicylic and citric acids as well as acid forming lactones such as gluconolactone and glucarolactone. Most preferred is citric acid. Also suitable as acid material may be encapsulated acids. Typical encapsulating material may include water soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7, preferably less than 6.5, optimally less than 5. These acids preferably at 25° C. are in solid form, i.e. having melting points no less than 25° C. Concentrations of the acid should range from about 0.5 to about 80%, preferably from about 10 to about 65%, optimally from about 20 to about 45% by weight of the total composition.

A second component of compositions within the pouch is that of an alkaline material. The alkaline material is a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). Preferably the alkaline material is sodium or potassium bicarbonate. Amounts of the alkaline material may range from about 1 to about 80%, preferably from about 5 to about 49%, more preferably from about 15 to about 40%, optimally from about 20 to about 35% by weight of the total composition.

By the term "anhydrous" is meant the presence of no more than about 15%, preferably no more than about 5% and optimally no more than 1% water by weight of the total composition. Water of hydration is not considered to be water for purposes of the anhydrous definition. However, it is preferred to minimize, preferably to eliminate any water of hydration.

Advantageously the combined amount of acidic and alkaline materials will be at least about 1.5%, preferably from about 40 to about 95%, optimally from about 60 to about 80% by weight of the total composition.

An optimal further component of compositions according to the present invention is that of a surfactant, preferably a dry surfactant solid at 20° C. Most suitable for the present invention is sodium cocoyl isethionate. Other useful surfactants include sodium methyl cocoyl taurate, sodium lauroyl sarcosinate and sodium lauryl sulfate. Surfactants may be of the anionic, cationic, nonionic, amphoteric, zwitterionic varieties and combinations thereof. Amounts of the surfactant may range from about 0.1 to about 30%, preferably from about 1 to about 30%, optimally from about 8 to about 20% by weight of the total composition.

A variety of skin benefit agents may be included to improve afterfeel properties. Advantageously these substances will be available as anhydrous dry powders. Alternatively these substances may be liquids deposited upon or into a powdered substrate (e.g. calcium silicate or zeolite) to achieve a resultant dry flowing powder. Within the skin benefit agent scope are several categories of materials. These include emollients, antiaging actives, antibacterials and fungicides, skin lighteners, sunscreens and combinations thereof. Amounts of the skin benefit agents may range from about 0.001 to about 40%, preferably from about 0.1 to about 20%, more preferably from about 0.5 to about 10%, optimally between about 1 and about 5% by weight of the total composition.

Emollients may be in the form of natural or synthetic esters, silicone oils, hydrocarbons, starches, fatty acids and mixtures thereof. Typically the emollient may range in concentration from about 0.1 to about 35% by weight of the total composition.

Silicone oils may be divided into the volatile and non-volatile variety. The term "volatile" as used herein refers to those materials which have a measurable vapor pressure at ambient temperature (25° C.). Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. white cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 22 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid ester, diethylene glycol mono- and di-fatty acid esters, polyethylene glycol (200–8000) mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

(6) Triglycerides such as sunflower seed oil, maleated sunflower seed oil, polycottonseedate, borage seed oil and safflower oil.

Hydrocarbons suitable as emollients include petrolatum, mineral oil, isoparaffins and hydrocarbon waxes such as polyethylene.

Starches are also suitable emollients. Typical of this class is tapioca and arabinogalactan.

Fatty acids may also be suitable as emollients. The fatty acids normally have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids.

Antiaging actives are also useful as skin benefit agents. Included within this category are vitamins, retinoids and combinations thereof. Amounts of these materials may range from about 0.001 to about 20% by weight of the total composition. Suitable vitamins include ascorbic acid, Vitamin $B_6$, Vitamin $B_{12}$, tocopherol as well as salts and $C_1$–$C_{20}$ esters thereof. Suitable retinoids include retinoic acid as well as its $C_1$–$C_{22}$ esters and salts, retinol and $C_1$–$C_{22}$ fatty esters of retinol including retinyl linoleate.

Another class of antiaging actives are the alpha- and beta-hydroxycarboxylic acids and salts thereof. Representative of this group are glycolic acid, lactic acid, malic acid, hydroxyoctanoic acid, salicylic acid and mixtures of these as well as their salts. Suitable salts are the alkalimetal, ammonium and $C_1$–$C_{10}$ alkanol ammonium salts.

Antibacterials and fungicidals may also be included as skin benefit agents. Representative of these categories are triclosan, tricloban, hexetidene, chlorhexadene, gluconates, zinc salts (e.g. zinc citrate and zinc phenolsulfonate) and combinations thereof.

Skin tighteners may also be included under the skin benefit agents. Typical of this category are niacinamide, kojic acid, arbutin, vanillin, ferulic acid and esters thereof, resorcinol, hydroquinone, placental extract and combinations thereof.

Sunscreens may also be included as skin benefit agents. Particularly preferred are such materials as ethythexyl p-methoxycinnamate, available as Parsol® MCX, avobenzene available as Parsol® 1789 and benzophenone-3, also known as Oxybenzone. Inorganic sunscreen actives may be employed such as microfine titanium dioxide, polyethylene and various other polymers. Amounts of the sunscreen agents may generally range from 0.1 to 30%, preferably from 2 to 20%, optimally from 4 to 10% by weight.

Adjunct functional agents may also be incorporated into compositions of the present invention. These include electrolytes, thickeners and mixtures thereof. Amounts of these substances may range from about 0.1 to about 20%, preferably from about 0.3 to about 10%, optimally between about 0.5 and about 5% by weight of the total composition.

Electrolytes may be selected from alkali, alkaline earth or ammonium salts of phosphates, silicates, halides, sulphates and mixtures thereof. Typical phosphates are potassium polymetaphosphate, sodium tripolyphosphate, sodium tetrapyrophosphate, sodium or potassium pyrophosphate and sodium hexametaphosphate. Most preferred is potassium polymetaphosphate available as Lipothix 100B® which is a 70:30 mixture of potassium polymetaphosphate and sodium bicarbonate, available from Lipo Chemicals, Inc., Paterson, N.J. Preferred sulphates are the magnesium sulphates.

Thickeners which may improve afterfeel properties on skin include inorganic or organic substances. A particularly preferred inorganic thickener is sodium magnesium silicate commercially available as Optigel SH®. Organic thickeners include alginic acid as well as sodium and calcium alginates, sodium carboxymethyl cellulose, hydroxypropyl methylcellulose, hydroxypropyl cellulose, hydroxyethyl cellulose and combinations thereof. Most preferred is alginic acid commercially available as Kelacid® from Sud-Chemie Rheologicals, Louisville, Ky. Alginic acid is highly effective at removing the slimy feel associated with deposits of alkaline material which are not fully rinsed away from the skin. Amounts of the thickener may range from about 0.1 to about 20%.

Polysaccharides useful in this invention are dry solid anhydrous substances such as sorbitol, sugars, (such as trehalose), starches, modified starches (e.g. aluminum octenyl succinate) and mixtures thereof. Most preferred is sorbitol.

Deposition aids may also be incorporated in compositions of the present invention. These assist in depositing skin benefit agents onto the skin surface. Particularly effective are cationic monomers and polymers for this purpose. Illustrative are the following: Lauryltrimethylammonium chloride; Stearyltri(2-hydroxyethyl) ammonium chloride; Lauryldimethylbenzylammonium chloride; Cetyldimethylbenzylammonium chloride; Cetylpyridinium chloride; Polydiallyldimethylammonium chloride; Diallydimethylammonium salt copolymerized with acrylamide; Guar hydroxypropyltrimonium chloride; Cationic hydroxyethylcellulosics; Cationic hydroxyethylcellulosics; Cetyltrimethylammonium chloride; Decyldimethyloctylammonium chloride; and Myristyltrimethylammonium chloride Most preferred for purposes of this invention are cationic guar gums such as Jaguar C13S® which is guar hydroxypropyltrimonium chloride and Polyquaternium 7 commercially available as Merquat 2200. Amounts of the deposition aid may range from about 0.01 to about 1%, preferably from about 0.05 to about 0.5%, optimally from about 0.1 to about 0.3% by weight.

Advantageously an emotive agent such as a fragrance and/or botanical extract are included with the effervescent cleansing composition. Fragrances and botanicals are often liquids. For this reason it may be necessary to uniformly distribute and allow absorption of liquid components into the solid powder. One method of best achieving this is to spray these liquids onto the solids. Amounts of the fragrance and/or botanicals combined may be at levels from about 0.1 to about 3%, preferably from 0.5 to 2%, optimally from 0.8 to 1.5% by weight of the total composition.

The term "fragrance" is defined as a mixture of odoriferous components, optionally mixed with a suitable solvent diluent or carrier, which is employed to impart a desired odor. Particular preferred odoriferous components are cyclic and acyclic terpenes and terpenoids. These materials are based upon isoprene repeating units. Examples include alpha and beta pinene, myrcene, geranyl alcohol and acetate, camphene, dl-limonene, alpha and beta phellandrene, tricyclene, terpinolene, allocimmane, geraniol, nerol, linanool, dihydrolinanool, citral, ionone, methyl ionone, citronellol, citronellal, alpha terpineol, beta terpineol, alpha fenchol, borneol, isoborneol, camphor, terpinen-1-ol, terpin-4-ol, dihydroterpineol, methyl chavicol, anethole, 1,4 and 1,8 cineole, geranyl nitrite, isobornyl acetate, linalyl acetate, caryophyllene, alpha cedrene, guaiol, patchouli alcohol, alpha and beta santalol and mixtures thereof. Botanicals of particular use in the present invention include yarrow, chamomile, jasmine, lavender, horse chestnut, sage, thyme, yucca, coltsfoot and mixtures thereof.

Preservatives can desirably be incorporated into the cosmetic compositions of this invention to protect against the growth of potentially harmful microorganisms. Suitable traditional preservatives for compositions of this invention are alkyl esters of para-hydroxybenzoic acids. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. Preservatives are preferably employed in amounts ranging from 0.01% to 2% by weight of the composition.

Colorants may also be included in compositions of the present invention. These substances may range from about 0.05 to about 5%, preferably between 0.1 and 3% by weight.

It is important that the webs are not readily torn open through consumer rubbing of the article. Unlike laundry sachet articles, pouches of the present invention should not rupture to allow dispersion of their granular contents into wash water. Rather it is intended for all composition components to exit by dissolution through the permeable walls of the pouch.

Skin surfaces against which articles of the present invention are useful include face, body, scalp, axilla and even legs/feet. When the article is a foot cleanser, it would be advantageous for the pouch on one of its sides to be coarse while the second of the substrates may be soft and gentle.

Except in the operating and comparative examples, or where otherwise explicitly indicated, all numbers in this description indicating amounts of material are to be understood as modified by the word "about".

The term "comprising" is meant not to be limiting to any subsequently stated elements but rather to encompass non-specified elements of major or minor functional importance. In other words the listed steps, elements or options need not be exhaustive.

The following examples will more fully illustrate embodiments of this invention. All parts, percentages and proportions referred to herein and in the appended claims are by weight unless otherwise indicated.

EXAMPLE 1

An effervescent cleansing composition was prepared according to the formulation reported in Table 1. Phase A was dry blended in a high speed shearing mixer. Fragrance was then sprayed onto the resultant powder as a Phase B. Three grams of the resultant powder are then placed into a pocket of a 5 cm by 8 cm oval pouch. Walls of the pouch are formed by heat sealing the circumferences of a non-woven spun lace web to a non-woven SMMS composite web. The spun lace web is a material whose fibers have been oriented in a direction perpendicular of the major axis of the pouch (i.e. in the cross direction).

TABLE I

| INGREDIENT | WEIGHT % |
|---|---|
| PHASE A | |
| Sodium Bicarbonate | 34.5 |
| Citric Acid (Anhydrous) | 40.4 |
| Sodium Cocoyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |

EXAMPLE 2

Another effervescent cleansing composition was prepared according to the formulation reported in Table II. The composition is then sealed into a pouch as described in Example 1.

TABLE II

| INGREDIENT | WEIGHT % |
|---|---|
| PHASE A | |
| Sodium Bicarbonate | 32.3 |
| Citric Acid (Anhydrous) | 41.1 |
| Sodium Cocoyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| Laracare A200 ® (Arabinogalactan) | 1.0 |
| Ascorbic Acid | 0.5 |
| PHASE B | |
| Fragrance | 1.0 |

EXAMPLE 3

A face cleansing effervescent composition was prepared according to the formulation reported in Table III. The composition is then sealed into a pouch as described in Example 1.

TABLE III

| INGREDIENT | WEIGHT % |
|---|---|
| PHASE A | |
| Sodium Bicarbonate | 33.6 |
| Citric Acid (Anhydrous) | 39.0 |
| Sodium Cocyl Isethionate (Powder) | 3.0 |
| Sodium Methyl Cocoyl Taurate | 6.0 |
| Sodium Lauryl Sulfate | 2.5 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 2.0 |
| Tapioca | 5.5 |
| Methyl Gluceth 20-Benzoate | 2.0 |
| Guar Hydroxypropyl Trimonium Chloride | 0.25 |
| PHASE B | |
| Fragrance | 0.65 |

EXAMPLE 4

A still further effervescent cleansing composition according to the present invention may be prepared according to the formulation reported under Table IV. The dry mixed ingredients at a weight level of 3.5 grams per sample are placed into a moon-shaped pouch as shown in FIG. 3 with lengths along major and minor (width) axis of 9 cm and 5.5 cm. The powdered sample is placed between a layer of spuntace web and an SMS layer to which a high loft sheet is sealed. The webs of spuntace and SMS are arranged to have their fibers oriented cross to the major axis direction. All sides of the pouch are welded by ultrasonic heat to ensure against powder escaping.

TABLE IV

| INGREDIENT | WEIGHT % |
|---|---|
| Anhydrous Citric Acid | 24.00 |
| Sodium Bicarbonate | 24.00 |
| Sodium Lauryl Sulfoacetate | 3.75 |
| Sodium Cocoyl isethionate | 3.75 |
| Polyquaternium 7 | 0.50 |
| Sodium C14–C16 Olefin Sulfonate | 3.75 |
| Guar hydroxypropyltrimonium Chloride | 0.40 |
| Ascorbyl Palmitate | 0.01 |
| Isocetyl Behenate | 5.00 |
| Sodium Stearoyl Lactylate | 3.00 |
| Disodium Dimethicone Copolyol Sulfosuccinate | 1.00 |
| Vitamin A Palmitate | 0.01 |
| Sodium Lauroyl Lactylate | 5.00 |
| PEG 8000 | 5.00 |
| Vitamin E | 0.40 |
| Calcium Silicate | 9.00 |
| Maltodextrin | 11.13 |
| Fragrance | 0.30 |

The foregoing description and drawing illustrate selected embodiments of the present invention. In light thereof, variations and modifications will be suggested to one skilled in the art, all of which are within the spirit and purview of this invention.

What is claimed is:

1. An article for cleansing surfaces, the article comprising:
    a curvilinear pouch formed from a plurality of walls, at least one of the walls being water permeable, and at least one of the walls being formed from at least one web of non-woven entangled fibers, the fibers being entangled in a direction perpendicular to a major longitudinal axis of the web; and
    wherein the pouch is neither square nor rectangular in shape an effervescent cleanser composition which is an anhydrous dry solid activable by water to generate gases, the composition being held within the pouch, and upon generation of gases the pouch walls billowing outwardly.

2. The article according to claim 1 wherein the entangled fibers are hydroentangled.

3. The article according to claim 1 wherein the at least one web has a cross and machine direction, and tensile strengths of the web in the cross and machine directions respectively being increased by at least 20% through orientation.

4. The article according to claim 1 wherein the at least one web is a nonwoven sheet selected from the group consisting of meltblown, spunbond and spunlace construction.

5. The article according to claim 1 wherein composition comprises from about 0.5 to about 80% by weight of an acid and from about 1 to about 80% by weight of an alkaline material.

6. The article according to claim 1 wherein the pouch is oval in shape.

7. The article according to claim 1 wherein the pouch is neither square nor rectangular in shape.

8. A method for cleansing body surfaces, the method comprising:
    (i) preparing an article comprising:
        a curvilinear pouch formed from a plurality of walls, at least one of the walls being water permeable, and at least one of the walls being formed from at least one web of non-woven entangled fibers, the fibers being entangled in a direction perpendicular to a major longitudinal axis of the web; and
    wherein the pouch is neither square nor rectangular in shape an effervescent cleanser composition which is an anhydrous dry solid activable by water to generate gases, the composition held within the pouch, and upon generation of gases the pouch walls billowing outwardly;
    (ii) wetting the article to generate an effervescent cleansing foam; and
    (iii) applying the wetted article with generated effervescent cleansing foam onto parts of a user's body surfaces and cleansing therewith those surfaces.

9. An article for cleansing body surfaces, the article comprising:
    an effervescent cleanser powdered composition capable of generating a foam upon contact with water, the composition being anhydrous and comprising;
    (i) from about 1 to about 80% of an alkaline material;
    (ii) from about 0.5 to about 80% of an acid material; and
    (iii) from about 0.1 to about 30% of a surfactant
    a curvilinear pouch formed from a plurality of walls, at least one of the walls being water permeable, and at least one of the walls being formed from at least one web of non-woven entangled fibers, the fibers being entangled in a direction perpendicular to a major longitudinal axis of the web, the composition being stored within the pouch.

* * * * *